United States Patent [19]

Orban et al.

[11] 3,960,875
[45] June 1, 1976

[54] PROCESS FOR THE PREPARATION OF 2,2,6,6-TETRAMETHYL-4-OXOPIPERIDINE

[75] Inventors: Ivan Orban, Basel; Hanns Lind, Liestal; Heimo Brunetti, Reinach; Jean Rody, Basel, all of Switzerland

[73] Assignee: Ciba-Geigy Corporation, Ardsley, N.Y.

[22] Filed: June 21, 1974

[21] Appl. No.: 481,935

[30] Foreign Application Priority Data

June 29, 1973 Switzerland............... 9506/73
Apr. 19, 1974 Switzerland............... 5540/74
May 22, 1974 Switzerland............... 7019/74

[52] U.S. Cl. ................................. 260/293.89
[51] Int. Cl.² ............................ C07D 211/74
[58] Field of Search .................... 260/293.89

[56] References Cited
UNITED STATES PATENTS
3,513,170    5/1970    Murayama et al.............. 260/294.7

*Primary Examiner*—G. Thomas Todd
*Attorney, Agent, or Firm*—Nestor W. Shust

[57] ABSTRACT

2,2,6,6-Tetramethyl-4-oxopiperidine is prepared from 2,2,4,4,6-pentamethyl-2,3,4,5-tetramethylpyrimidine (acetonine) by heating in the presence of acetone, di-acetone alcohol or water. These regents may be used in excess or an organic solvent is added. The preferred modification is the heating of acetonine hydrate in an excess of acetone or in an acetone-methanol mixture to about 40° to 65°C for several hours. The use of di-acetone alcohol permits higher reaction temperatures leading to shorter reaction times.

19 Claims, No Drawings

PROCESS FOR THE PREPARATION OF 2,2,6,6-TETRAMETHYL-4-OXOPIPERIDINE

The preparation of 2,2,6,6-tetramethyl-4-oxopiperidine is already known. It comprises the reaction of 2,2,4,4,6-pentamethyl-2,3,4,5-tetrahydropyrimidine with a Lewis acid in the presence of water, as according to DT-OS 1,695.753.

On the basis of this prior art, the present invention relates to a process wherein 2,2,6,6-tetramethyl-4-oxopiperidine is prepared from 2,2,4,4,6-pentamethyl-2,3,4,5-tetrahydropyrimidine (acetonine by a process in which the acetonine is heated
   a. without water, or with less than the equimolar amount of water, relative to the acetonine, and in the presence of acetone and/or diacetone alcohol, or
   b. with at least the equimolar amount of water, relative to the acetonine.

The reaction according to (b) can be performed in the presence of acetone and/or diacetoneamine, triacetonediamine and/or an acid condensation product of acetone. An acid condensation product of acetone is, e.g. phorone and, in particular, mesityl oxide, and more especially diacetone alcohol.

An organic solvent can be advantageously used in the reaction according to the invention. Organic solvents particularly suitable for the process according to the invention are, e.g.: hydrocarbons such as aromatic hydrocarbons, e.g. benzene, toluene and xylene, as well as aliphatic hydrocarbons such as hexane, heptane and cyclohexane, also chlorinated hydrocarbons such as methylene chloride, trichloroethane, carbon tetrachloride, chloroform, ethylene chloride and chlorobenzene, as well as ethers such as tetrahydrofuran, dioxane and diethyl ether, also nitriles such as acetonitrile, and aprotic polar solvents such as sulpholane, nitromethane, dimethylformamide, dimethylacetamide, tetramethylurea, hexamethylphosphoric acid amide, and dimethylsulphoxide, and, particularly preferred, alcohols such as mono- or polyfunctional, unsubstituted or substituted, aliphatic alcohols, e.g. lower alkanols such as methanol, ethanol, propanol, iso-propanol and tert.-butanol, as well as cyclohexanol, benzyl alcohol, ethylene glycol monomethyl ether, glycol and propane-1,3-diol, and also acetone. Expecially suitable is a $C_1$–$C_4$-alcohol, such as methanol and/or particularly acetone, diacetone alcohol, mesityl oxide, phorone, diacetoneamine, triacetonediamine, as well as mixtures of such solvents. Particularly suitable are: alcohols such as methanol or ethanol, ethers such as ethylene glycol monomethyl ether, or ketones such as acetone. Acetone or methanol or mixtures thereof are preferably used. Equally preferably used is diacetone alcohol.

Compared with processes known from prior art, this process has the advantage that, in a surprising manner, a good yield of product is obtained without catalyst.

The reaction is performed at elevated temperature, for example, between 40° and 120°C, particularly, between 40° and 95°C. In the presence of acetone, the preferred reaction temperature is 40°–65°C, particularly between 50° and 55°C; in the presence of diacetone alcohol or mesityl oxide it is 80°–100°C.

The reaction time is preferably ½–15 hours, particularly 1–12 hours; with acetone as co-reactant preferably 7–14 hours, and with diacetone alcohol as co-reactant preferably ½–2 hours, especially 1–1½ hours.

The course of the reaction is favourably influenced by pressure, e.g. by 1–30, particularly 1–10, but more especially by 1–3 atmospheres excess pressure.

The amount of acetone, diacetoneamine, triacetonediamine or condensation product to be used is at least 1.5 mol per mol of pyrimidine starting material; it can however be up to 10 moles. For practical reasons, the preferred range is 2 to 6 mol, especially 3 to 4 mol. It is also possible however to use with advantage less than 1.5 mol.

The use of diacetone alcohol as co-reactant is particularly suitable, since the reaction can be more rapidly preformed because of the possibility of a higher reaction temperature.

Processing can be carried out in a manner known per se, e.g. by addition of water and separation as hydrate, or by addition of acid, such as hydrochloric acid, sulphuric acid or oxalic acid, and separation as salt, or by addition of an excess of liquor, especially concentrated liquor, such as aqueous sodium hydroxide solution or potassium hydroxide solution, and separation as organic layer, or particularly by distillation.

In the reaction according to the invention it is advantageous to use an amount of water, as pyrimidine-hydrate water and/or as a small amount of added water. The water-releasing agent can in general also be a hydrate of a salt.

The present invention is illustrated by the following examples.

EXAMPLE 1

A mixture of 250 g of 2,2,4,4,6-pentamethyl-2,3,4,5-tetrahydropyrimidine hydrate, 100 g of acetone and 100 g of methanol is refluxed for 13 hours. The solution is subsequently concentrated in vacuo, and the oil remaining is distilled in vacuo. The yield is 185 g of a slightly yellowish oil, B.P.$_{12}$ = 80°–86°C, which, after the addition of about 22 ml of water, solidifies to form crystals of 2,2,6,6-tetramethyl-4-oxopiperidine-hydrate.

EXAMPLE 2

43 g of acetonine hydrate, 75 g of acetone and 10 g of ethanol are stirred for 12 hours at 55°C. After the solvent has been evaporated off, the residue is fractionated in vacuo to give 32 g of triacetoneamine (B.P. 72°–74°/5 Torr), which corresponds to a yield of 82%.

EXAMPLE 3

43 g of acetonine hydrate, 75 g of acetone and 10 g of benzene are stirred for 12 hours at 55°. The solvent is evaporated off and the residue fractionated in vacuo. There is obtained 25 g of triacetoneamine (B.P. 72°–74°/5 Torr), which corresponds to a yield of 64%.

EXAMPLE 4

43 g of acetonine hydrate, 75 g of acetone and 10 g of ethylene glycol monomethyl ether are stirred for 12 hours at 55°. Processing according to Example 4 produces 31 g of triacetoneamine, which corresponds to a yield of 80%.

If, instead of 10 g of ethylene glycol monomethyl ether, 20 g of dimethylformamide is added to the above-mentioned mixture of acetonine hydrate and acetone, the procedure otherwise being as described, then triacetoneamine is obtained likewise with ca. 80% yield.

EXAMPLE 5

10 g of acetonine hydrate and 10 g of diacetone alcohol are heated to about 100°. At regular intervals of time, the content of acetonine and triacetone, respectively, in the reaction mixture is determined by gas-chromatography. After a reaction time of 2 hours at 90°–100°C, less than 3% of the original amount of acetonine is detectable. The remainder has been coverted to triacetoneamine, which is isolated by fractional distillation.

EXAMPLE 6

10 g of anhydrous acetonine and 10 g of diacetone alcohol are heated to about 100°C. At regular intervals of time, the amount of acetonine and triacetoneamine, respectively, contained in the reaction mixture is determined by gas-chromatography. After a reaction time of 4 hours at 90°–100°C, less than 5% of the original amount of acetonine is detectable. The remainder has been to a great extent converted to form triacetoneamine, which is isolated by fractional distillation.

EXAMPLE 7

15.4 g of anhydrous acetonine and 20 g of acetone are refluxed for 24 hours. After this period of reaction, a gas-chromatographical examination of the reaction mixture shows that about 80% of triacetoneamine, relative to the amount of acetone used, has been formed. The triacetoneamine is isolated by distillation.

If there is additionally added to the above-mentioned reaction mixture 0.9 g of water, the procedure being otherwise as described there, then an approximately equally good conversion of acetonine into triacetoneamine is obtained.

EXAMPLE 8

17.2 g of acetonine hydrate, 20 g of acetone and 1.8 g of water are refluxed for 24 hours. After this time of reaction, an examination by gas-chromatography of the reaction mixture shows that about 80% of triacetoneamine, relative to the amount of acetonine used, has been formed.

If, instead of 1.8 g of water, 3.6 g or 5.4 g of water is added to the above mixture of acetonine hydrate and acetone, with the procedure otherwise as described there, then triacetoneamine is obtained with approximately the same yields.

EXAMPLE 9

17.2 g of acetonine hydrate and 30 g of acetone are heated in a sealed tube for 24 hours at 45°C. After this period of reaction, it is shown by gas-chromatographical examination of the reaction mixture that at least 85% of triacetoneamine, relative to the amount of acetonine used, has been formed. The triacetoneamine is isolated by distillation.

What we claim is:

1. Process for the preparation of 2,2,6,6-tetramethyl-4-oxopiperidine from 2,2,4,4,6-pentamethyl-2,3,4,5-tetrahydropyrimidine (acetonine), wherein acetonine is heated
    a. without water or with less than the equimolar amount of water, relative to the acetonine, and in the presence of acetone and/or diacetone alcohol, or
    b. with at least the equimolar amount of water, relative to acetonine.
2. Process according to claim 1, wherein the reaction is performed in the presence of an organic solvent or solvent mixture.
3. Process according to claim 2, wherein the solvent used is acetone, diacetone alcohol, mesityl oxide, diacetoneamine, triacetonediamine, phorone, a $C_1$–$C_4$-alcohol, ethylene glycol monomethyl ether, or mixtures thereof.
4. Process according to claim 3, wherein the $C_1$–$C_4$-alcohol is methanol.
5. Process according to claim 3, wherein the solvent is acetone.
6. Process according to claim 3, wherein the solvent is diacetone alcohol.
7. Process according to one of claims 1, wherein the reaction is performed under elevated pressure, such as 1–30, particularly 1–10, and more especially 1–3 atmospheres.
8. Process according to claim 1b, wherein the applied ratio of acetonine to water is 1:1 to 1:5.
9. Process according to claim 1b, wherein the reaction is performed in the presence of acetone and/or diacetoneamine, triacetonediamine and/or an acid condensation product of acetone.
10. Process according to claim 9, wherein the employed acid condensation product of acetone is diacetone alcohol and/or mesityl oxide.
11. Process according to claim 1, wherein the reaction is performed at a temperature of between 40° and 120°C.
12. Process according to claim 9, wherein the reaction is performed in an organic solvent.
13. Process according to claim 1, wherein 2,2,4,4,6-pentamethyl-2,3,4,5-tetrahydropyrimidine-hydrate is heated with acetone.
14. Process according to claim 13, wherein the mixture is heated at 40°–65°C.
15. Process according to claim 9, wherein the organic solvent used is an acetone/methanol mixture.
16. Process according to claim 13, wherein an acetone/methanol mixture is used instead of acetone.
17. Process according to claim 9, wherein the reaction is performed in the presence of diacetone alcohol.
18. Process according to claim 17, wherein the reaction is performed at 80°–100°C.
19. Process according to claim 1, wherein stage (a) of the process is performed in the presence of acetone.

* * * * *